United States Patent
Odanaka et al.

[11] Patent Number: 6,074,342
[45] Date of Patent: Jun. 13, 2000

[54] HARD ENDOSCOPE USED FOR ASSISTING MICRO-OPERATION

[75] Inventors: Kunio Odanaka; Kunihiko Miyagi, both of Tokyo, Japan

[73] Assignee: Machida Endoscope Co., Ltd., Japan

[21] Appl. No.: 09/198,973

[22] Filed: Nov. 24, 1998

[30] Foreign Application Priority Data

Nov. 27, 1997 [JP] Japan ................................. 9-342057

[51] Int. Cl.⁷ ........................................................ A61B 1/06
[52] U.S. Cl. ........................ 600/164; 600/102; 600/138; 600/160
[58] Field of Search ........................... 600/102, 109, 600/130, 138, 160, 164, 179; 359/434, 435

[56] References Cited

U.S. PATENT DOCUMENTS

| 3,257,902 | 6/1966 | Hopkins . | |
|---|---|---|---|
| 3,261,351 | 7/1966 | Wallace | 600/164 |
| 3,994,557 | 11/1976 | Hopkins | 600/156 |
| 4,248,213 | 2/1981 | Landre | 359/374 |
| 4,517,963 | 5/1985 | Michel | 600/126 |
| 4,576,147 | 3/1986 | Hashiguchi | 600/129 |
| 5,601,549 | 2/1997 | Miyagi . | |

FOREIGN PATENT DOCUMENTS

| 0712600 | 5/1996 | European Pat. Off. . |
|---|---|---|
| 190703 | 4/1906 | Germany . |
| 473166 | 2/1929 | Germany . |
| 1797127 | 4/1982 | Germany . |
| WO 9632052 | 10/1996 | WIPO . |

*Primary Examiner*—Linda C. M. Dvorak
*Assistant Examiner*—Brad C. Blaise
*Attorney, Agent, or Firm*—Eugene Stephens & Associates

[57] ABSTRACT

A hard endoscope used for assisting a micro-operation includes a body and an insert portion extending from the body. The insert portion includes a first linear portion, and a second linear portion longer than the first linear portion. The first and second linear portions are arranged forwardly in order from the body. A connecting portion is disposed between the first linear portion and the second linear portion. The insert portion thus constructed exhibits a bent configuration. The first and second linear portions have a first and a second relay lens, respectively, therein. The connecting portion has a prism therein. This prism transmits the light coming through the first relay lens to the second relay lens.

6 Claims, 4 Drawing Sheets

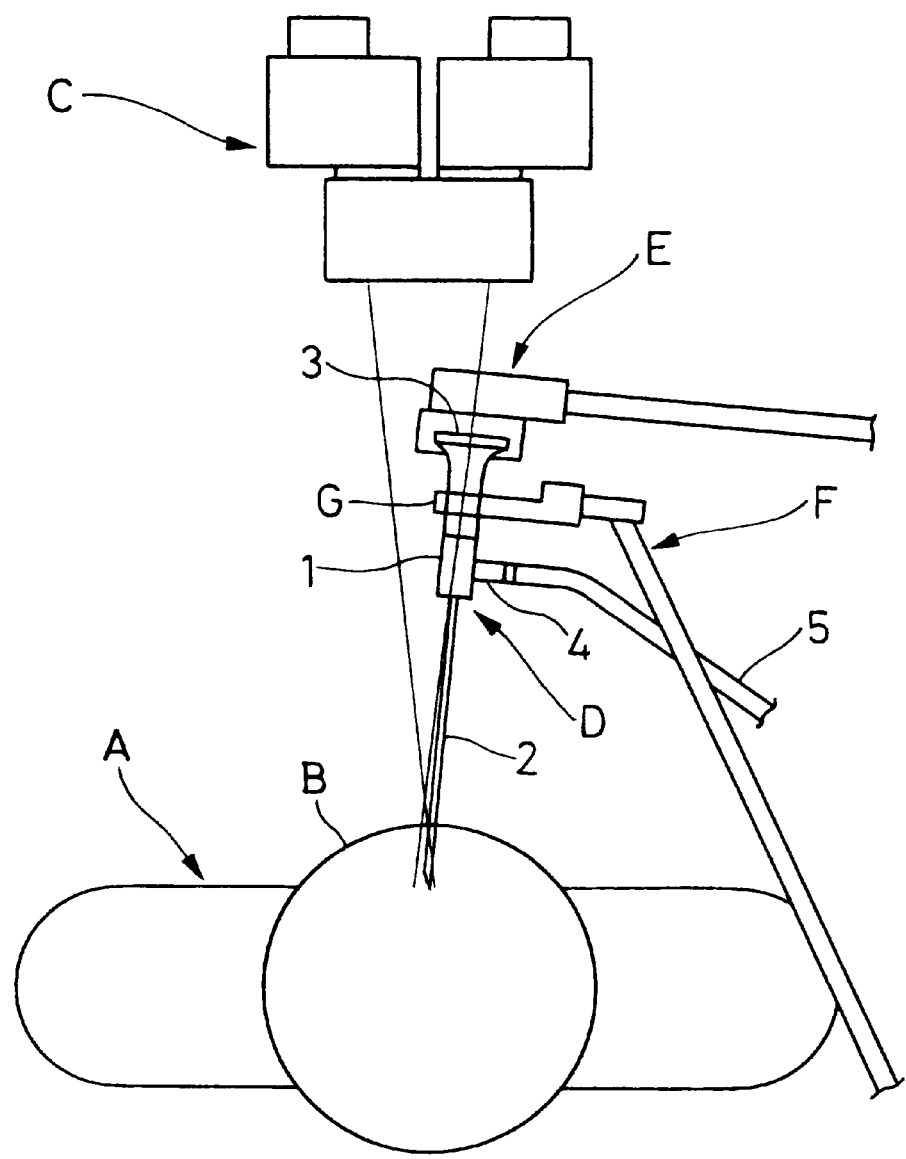

HARD ENDOSCOPE USED FOR ASSISTING MICRO-OPERATION

BACKGROUND OF THE INVENTION

This invention relates to a hard endoscope used as an auxiliary instrument when a surgical operation is carried out using a microscope.

Heretofore, when an operation is carried out with respect to a human brain, it is customary that a microscope C and an endoscope D are placed generally right above the head B (diseased part) of a patient A, as shown in FIG. 5. The endoscope D includes a body 1 and a hard insert portion 2 extending from the body 1. The insert portion 2 is provided on a distal end thereof with an objective lens and a plurality of relay lenses axially arranged side by side. The body 1 extends axially of the insert portion 2 and is provided on a rear end thereof with an ocular portion 3. An ocular lens is disposed in the ocular portion.

A camera E having a CCD (image sensor) is detachably attached to the ocular portion 3. A joint 4 projects from a distal end portion of the body 1. This joint 4 extends in a direction orthogonal to the axis of the body 1. A light guide cable 5 is connected to the joint 4. A bundle of optical fibers for transmission of illumination light reaches an illumination window formed on the distal end of the insert portion 2, through the light guide cable 5, the body 1 and the insert portion 2.

An intermediate portion of the body 1, i.e., the area of the body 1 between the ocular portion 3 and the joint 4, is firmly held by a chuck portion G at a distal end of a holding instrument F. By this, the endoscope D is supported in a predetermined position.

In the endoscope D having the above construction, the distal portion of the insert portion is inserted through a hole formed in the head B of the patient A, so that an image of the patient's brain, for example, side-view image, can be obtained. The image obtained by the endoscope D is photographed by the camera E and displayed in a monitor television in the form of a video image. The operator can carry out the operation while observing a magnified image of the brain obtained by the microscope C and further observing, where necessary, the side-view brain displayed in the monitor television.

However, since the insert portion 2 of the endoscope D thus constructed is inserted into the head B of the patient A in its generally vertical orientation, the body 1 and the camera E are brought into view field of the microscope C, thus disturbing the observation through the microscope C. If the body 1 should be brought out of the view field of the microscope C by declining the insert portion 2 in order for the body 1 not to disturb the operator's observation through the microscope C, a desired observation image could not be obtained, in some cases, by the endoscope D.

Another example of the endoscope used for assisting a micro-operation is disclosed in U.S. Pat. No. 5,601,549.

SUMMARY OF THE INVENTION

It is, therefore, an object of the present invention to provide a hard endoscope used for assisting a micro-operation, which endoscope does not disturb the operator's observation through a microscope.

In a hard endoscope according to the present invention, an insert portion, having a first and a second linear portion, exhibits a bent-configuration. Owing to this structural feature, the body can be brought out of the view field of a microscope. The first and second linear portions each include a relay lens therein, and a prism is placed in a connecting portion between the first linear portion and the second linear portion. Accordingly, a clear observation image can be obtained.

BRIEF DESCRIPTION OF THE DRAWING

FIG. 5 is a schematic view showing the conventional hard endoscope, wherein a brain operation using a microscope is undergoing with the help of the hard endoscope.

DETAILED DESCRIPTION OF THE EMBODIMENT

One embodiment of the present invention will now be described with reference to FIGS. 1 to 4.

Figure 1:
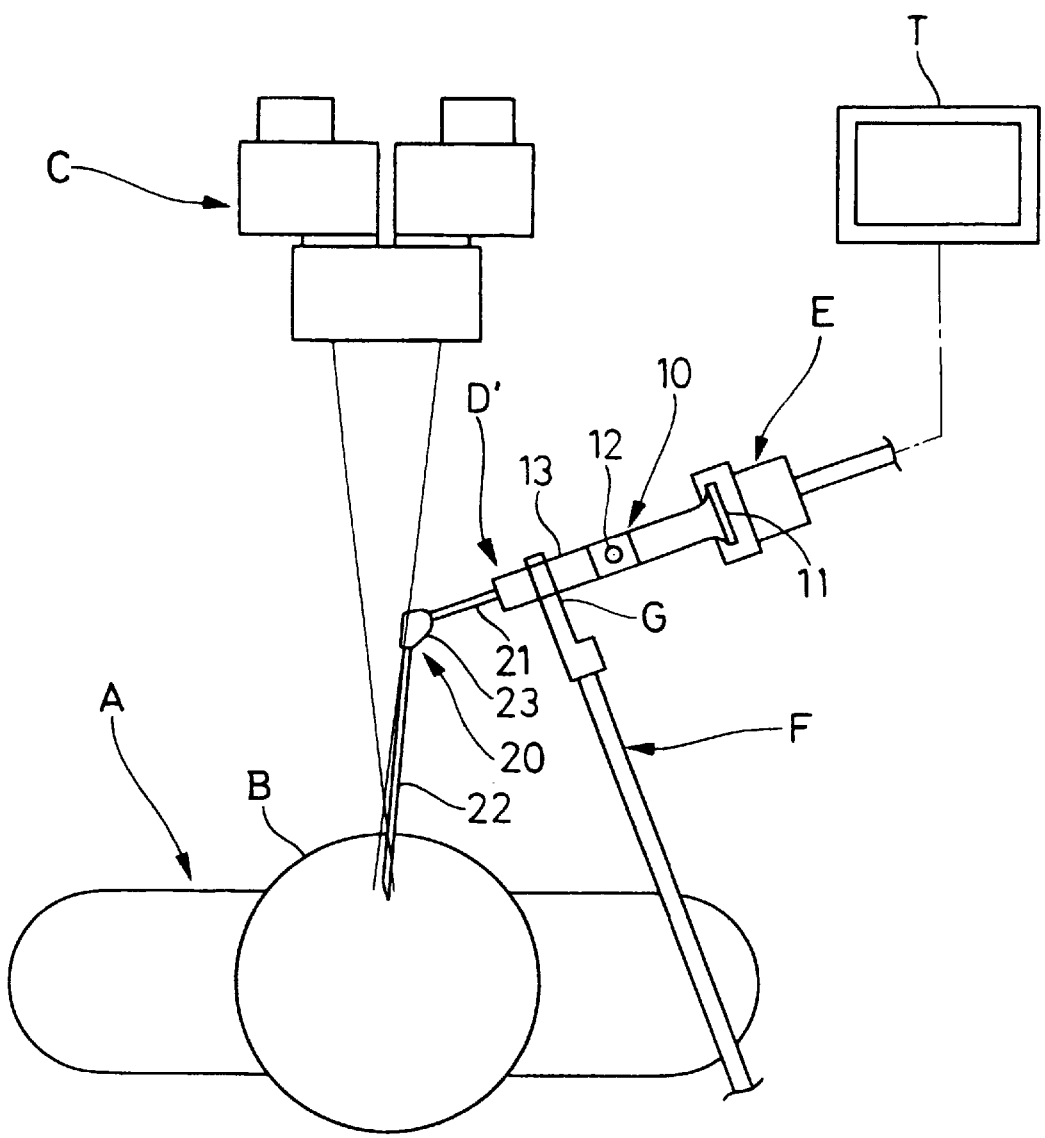
FIG. 1 is a schematic view showing a hard endoscope according to one embodiment of the present invention, wherein a brain operation using a microscope is undergoing with the help of the hard endoscope.
Figure 2:
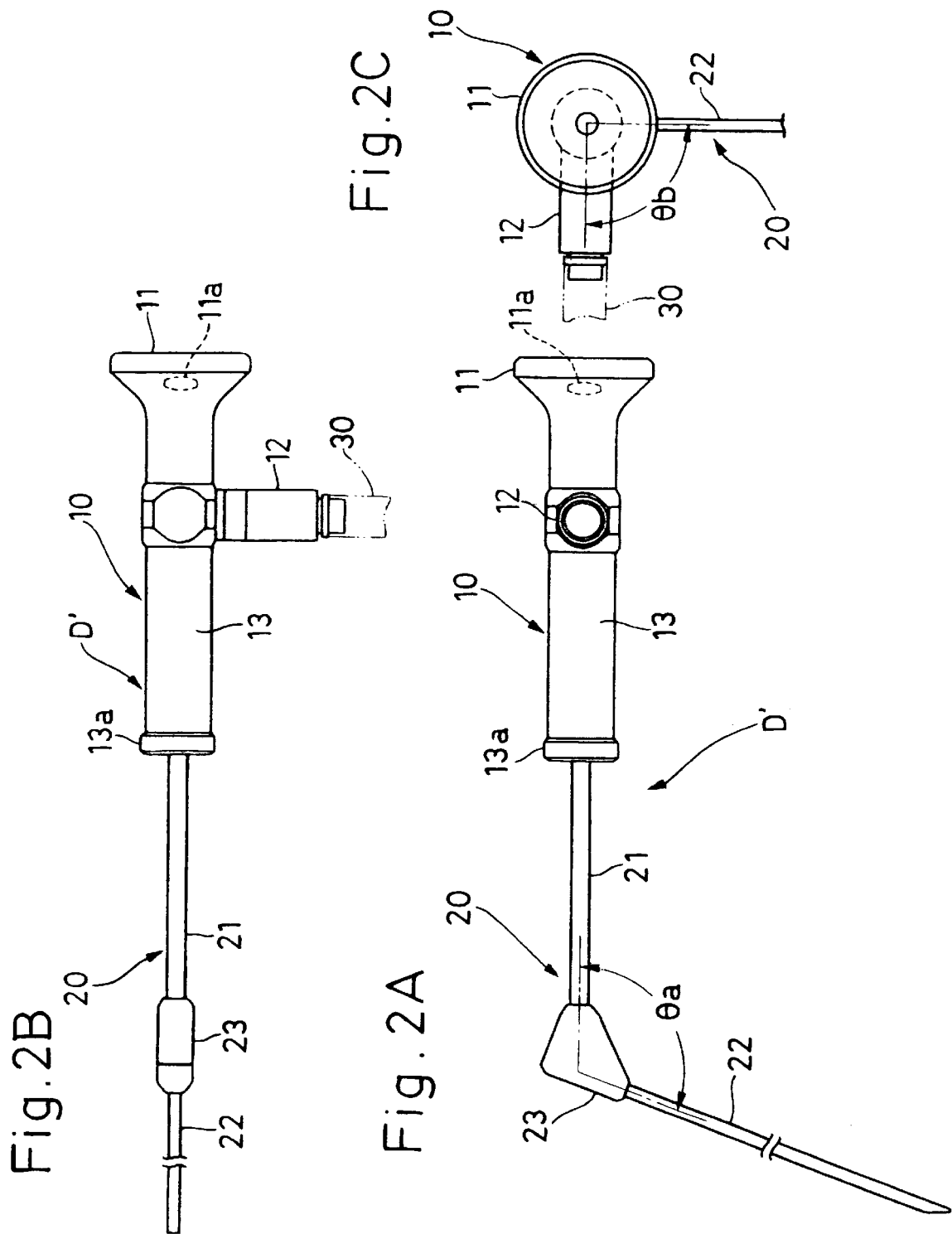
FIG. 2A is a front view showing an overall construction of the endoscope.
FIG. 2B is a plan view and FIG. 2C is a side view when viewed from a direction of an ocular side.

As shown in FIGS. 1 and 2, an endoscope D' includes a body 10 and an insert portion 20 extending from the body 10. The insert portion 20 includes a first linear portion 21 and a second linear portion 22 arranged forwardly in order from the body 10. The first and second linear portions 21, 22 are mutually crossed and connected together through a connecting portion 23. Owing to the forgoing, the insert portion 20 is bent at an intermediate portion thereof. A cross angle θ a (see FIG. 2A) between the first linear portion 21 and the second linear portion 22 is preferably from 90 degrees to 150 degrees, and more preferably from 100 degrees to 120 degrees. In this embodiment, the cross angle is 110 degrees. The first linear portion 21 is shorter than the second linear portion 22.

The body 10 extends axially of the first linear portion 21 of the insert portion 20 and exhibits a sleeve-like configuration. The body 10 is provided on a rear end thereof with an ocular portion 11 (receiving portion) having therein an ocular lens 11a. The body 10 has a joint portion 12 projecting orthogonally from an intermediate portion of the body 10. A front end portion between the insert portion 20 and the joint portion 12 of the body 10 is provided as a cylindrical grip portion 13. The grip portion 13 has an annular stopper 13a formed on a front end thereof. This stopper 13a is slightly larger in diameter than the grip portion 13.

Figure 3:
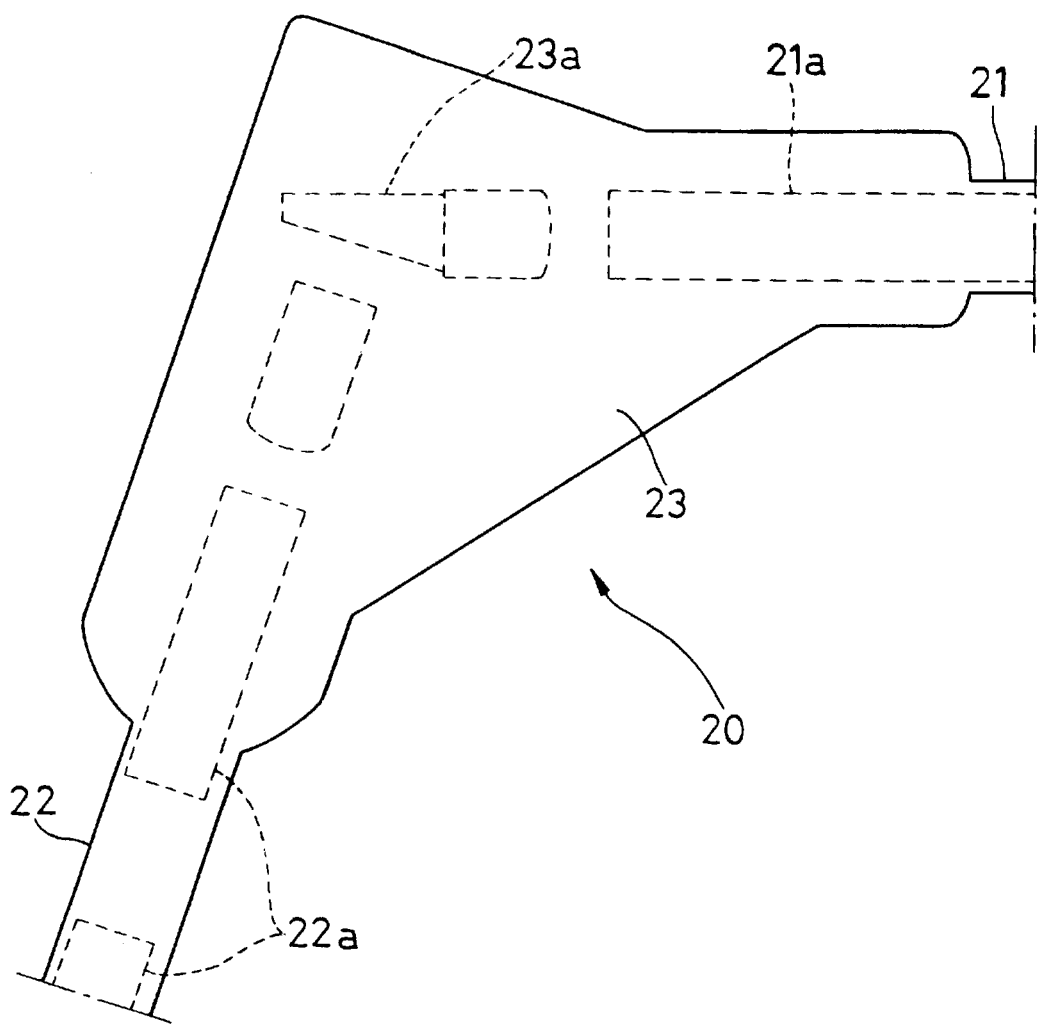
FIG. 3 is an enlarged front view showing a bent-portion of an insert portion.

A plurality of bar-like relay lenses 21a (only one is shown in FIG. 3) arranged side by side axially of the first linear portion 21 of the insert portion 20 are placed within the first linear portion 21. Those relay lenses 21a are optically connected, through a relay lens placed within the body 10, to the ocular lens 11a which is disposed backwardly thereof.

The second linear portion 22 of the insert portion 20 also includes a plurality of bar-like relay lenses 22a arranged side by side axially of the second linear portion 22.

The connecting portion 23 of the insert portion 22 has a prism 23a for optically connecting the relay lenses 21a, 22a together.

Figure 4:
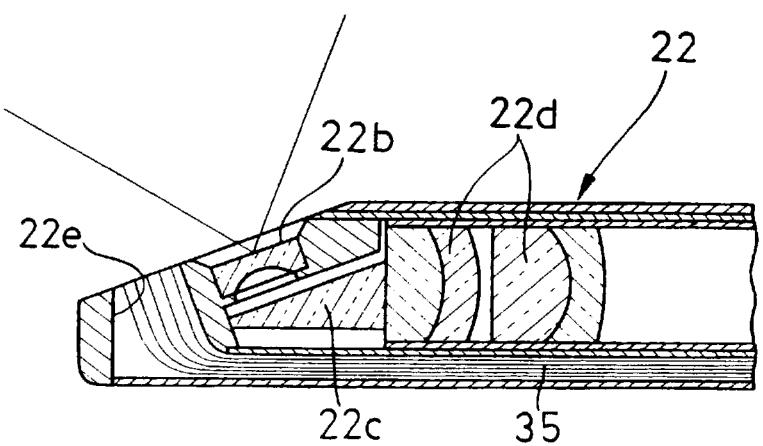
FIG. 4 is an enlarged sectional view showing an internal structure of a distal end portion of the insert portion.

As shown in FIG. 4, an observation window 22b for the purpose of side viewing is formed on a distal end portion of the second linear portion 22 of the insert portion 20. This observation window 22b is optically connected, through a prism 22c, to an objective lens 22d and to the relay lenses 22a which are disposed backwardly of the objective lens 22d. The view field direction from the observation window 22b is crossed with the axis of the second linear portion 22.

As shown in FIGS. 2(B) and 2(C), one end of a light guide cable 30 is connected to the joint portion 12 of the body 10. An optical fiber bundle 35 (only shown in FIG. 4) for the transmission of illumination light extends through the light guide cable 30 and further through the body 10 and the insert portion 20. A leading end of the optical fiber bundle 35 reaches an illumination window 22e formed on the distal end portion of the second linear portion 22.

As shown in FIG. 2(C), the second linear portion 22 and the joint portion 12 are not in alignment with each other, i.e., they extend in different directions when viewed axially of the first linear portion 21 of the insert portion 20. A cross angle θ b between the second linear portion 22 and the joint portion 12 is preferably 45 degrees or more. In this embodiment, the cross angle θ b is 90 degrees.

As shown in FIG. 1, for the use in a brain operation, a camera E having a CCD (image sensor) is detachably attached to the ocular portion 11 of the endoscope D'. Then, the second linear portion 22 of the insert portion 20 of the endoscope D' is brought into a generally vertical posture and the distal portion of the second linear portion 22 is inserted into the head B of a patient A. In that state, the grip portion 13 of the body 10 is gripped by a chuck portion G on a distal end of a holding instrument F such as a stand so that the endoscope D' is supported in a stable manner.

Operation of the endoscope D' will now be described in detail. Illumination light incoming to a basal end of the optical fiber bundle 35 is irradiated to the patient's brain as an object to be observed, through the illumination window 22e. The light reflected from the brain (a) enters the observation window 22b of the second linear portion 22 of the insert portion 20, (b) passes through the prism 22c, the objective lens 22d and the relay lens 22a, (c) converted in optical axis by the prism 23a at the connecting portion 23, (d) passes through the relay lenses 21a placed in the first linear portion 21 and the body 10, and (e) finally reaches the ocular lens 11a of the body 10. A magnified side-view image thus obtained by the endoscope D' is photographed by the CCD camera E.

The magnified side-view image obtained by the CCD camera E is displayed in a monitor television T connected to the CCD camera E. The operator carries out a brain operation while observing the magnified front-view image through the microscope C and also observes the magnified side-view image, by watching the monitor television T as needed, whereby a brain operation can be carried out in an accurate manner.

A small-sized monitor television, instead of the monitor television T, may be connected to the CCD camera E. This small-sized monitor television is built in the microscope C. The operator can carry out the brain operation while observing the magnified front image obtained by the microscope and the magnified side-view image in the small-sized television appearing in a location offset from the center of the view field of the microscope.

Since the light reflected from the object to be observed is transmitted through the relay lenses 21a, 22a and the prism 23a, (instead of through the optical fiber bundle) in the endoscope D', a clear observation image can be obtained.

Since the insert portion 20 of the endoscope D' is bent at its intermediate portion and the first linear portion 21 extends in a direction away from the view field of the microscope C, the body 10 connected to the basal end of the first linear portion 21 is out of the view field of the microscope C and therefore, the body 10 does not disturb the observation through the microscope C. By this, the operator can smoothly carry out a brain operation on the basis of the wide view field. Since the angle of insertion of the second linear portion 22 of the insert portion 20 into the head B of the patient A can be set freely without taking into consideration the relation between the body 10 and the view field of the microscope C, a desired image can be obtained.

Since the front end portion of the body 10 is defined by the grip portion 13 which is to be gripped by the chuck portion G on the distal end of the holding instrument F, the light guide cable 30 and the joint portion 12 do not disturb the smooth gripping work. The chuck portion G on the distal end of the holding instrument F is prevented from escaping by the stopper 13a on the front end of the grip portion 13.

Since the cross angle θb between the second linear portion 22 and the joint portion 12 is 90 degrees when viewed axially of the first linear portion 21 of the insert portion 20, the light guide cable 30 is not allowed to extend downwardly from the body 10 and therefore, the light guide cable 30 can be kept away from the head B of the patient A. As a consequence, a smooth operation can be carried out.

The second linear portion 22 is dimensioned long enough to keep the body 10 away from the diseased part. In contrast, the first linear portion 21 is preferably short in order to support the second linear portion 22 in a stable manner, with the body 10 held by the holding instrument F. The length of the first linear portion 21 is sufficient to move the body 10 away from the view field of the microscope C.

The present invention is not limited to the above embodiment but various modifications can be made. The cross angle θb between the second linear portion 22 and the joint portion 12 is not limited to 90 degrees of the above embodiment but it may be 180 degrees, for example.

The endoscope is not limited to the type designed for side view but it may be of the type designed for straight view (i.e., of the type having a view field in the axial direction of the second linear portion 22).

Since the ocular lens 11a is placed within the body 10 in the above embodiment, the operator can observe the image obtained by the endoscope D' directly from the ocular portion 11 and without through the camera E and the monitor television T. However, it is also accepted that instead of the ocular lens 11a, a lens capable of forming an image directly on the CCD of the camera E can be placed within the body 10.

The present invention is not limited to endoscopes of the type used for a brain surgical operation but it may likewise be applied to any type of endoscope which is normally utilized together with a microscope.

What is claimed is:

1. A hard endoscope used for assisting a micro-operation comprising:

(a) a body;

(b) a hard insert portion extending from a front end portion of said body, said insert portion having an illumination window and an observation window both formed on a distal end portion thereof; and (c) an optical fiber bundle for transmission of illumination light, a leading end of said optical fiber bundle being located at said illumination window and extending through said insert portion and said body so as to be led out of said body;

wherein said insert portion comprises:
- (i) a first and a second linear portion arranged forwardly in order from said body, said first and second linear portions being crossed with each other, said first and second linear portions including therein a first relay lens and a second relay lens, respectively, said second linear portion having an objective lens placed within a distal end portion thereof between said observation window and said second relay lens;
- (ii) a connecting portion for connecting said first and second linear portions together, said connecting portion including therein a prism; and
- (iii) an imaging transmitting optical path including said second relay lens, said prism and said first relay lens, wherein a joint portion projects from said body, a light guide cable is connected to said joint portion, and said optical fiber bundle extends through said joint portion and said light guide cable; and wherein said second linear portion and said joint portion are generally orthogonal to each other when viewed axially of said first linear portion of said insert portion.

2. The hard endoscope according to claim 1, wherein said second linear portion is longer than said first linear portion.

3. The hard endoscope according to claim 1, wherein said observation window has a view field in a direction crossing an axis of said second linear portion.

4. The hard endoscope according to claim 1, wherein said body extends axially of said first linear portion, a portion of said body located forwardly of said joint portion is provided as a grip portion, and there is a provision of a holding instrument which has a chuck portion formed on a distal end thereof, said chuck portion gripping said grip portion of said body.

5. The hard endoscope according to claim 4, wherein said grip portion is cylindrical and has an annular stopper formed on a front end thereof, said stopper being larger in diameter than the grip portion.

6. The hard endoscope according to claim 1, wherein a rear end portion of said body is provided as a receiving portion to which a camera connected to a monitor television is detachably attached.

* * * * *